United States Patent [19]

Hobo et al.

[11] Patent Number: 4,597,431

[45] Date of Patent: Jul. 1, 1986

[54] MELTING AND PRESSURE CASTING DEVICE

[75] Inventors: Sumiya Hobo, Tokyo; Toshio Shimizu; Masaru Nishida, both of Kyoto, all of Japan

[73] Assignee: Kyocera Corporation, Japan

[21] Appl. No.: 686,292

[22] Filed: Dec. 26, 1984

[30] Foreign Application Priority Data

Dec. 28, 1983 [JP] Japan ............................. 58-246548
May 24, 1984 [JP] Japan ............................. 59-106008

[51] Int. Cl.⁴ ........................................... B22D 18/00
[52] U.S. Cl. ................... 164/253; 164/258; 164/338.1; 164/335
[58] Field of Search ............ 164/335, 258, 256, 259, 164/338.1, 250.1, 513, 514, 492, 253; 501/88

[56] References Cited

U.S. PATENT DOCUMENTS

| | | | |
|---|---|---|---|
| 1,070,500 | 8/1913 | Mackenzie | 164/258 |
| 2,003,625 | 6/1935 | Boyer | 501/88 |
| 2,171,778 | 9/1939 | Yantis | 164/335 |
| 2,782,475 | 2/1957 | Wilhelm et al. | 164/256 |
| 3,404,202 | 10/1968 | Carlson et al. | 501/88 |
| 3,675,709 | 7/1972 | Vogerl et al. | 164/335 |
| 3,841,384 | 10/1974 | Tingquist et al. | 164/335 |
| 4,247,735 | 1/1981 | Rigatti-Luchini | 164/258 |

FOREIGN PATENT DOCUMENTS

2553807 11/1976 Fed. Rep. of Germany ...... 164/256

*Primary Examiner*—Nicholas P. Godici
*Assistant Examiner*—Samuel M. Heinrich
*Attorney, Agent, or Firm*—Spensley Horn Jubas & Lubitz

[57] ABSTRACT

A melting and pressure casting device characterized in that it comprises a cylindrical electric heating means set in a closed chamber reducible and increasable in gas pressure, a vertically long crucible set in the heating means, a mold provided below the crucible and connected thereto, and an upper sprue communicating between the lower portion of the pouring cup and the sprue formed in the mold, wherein the melt for casting is held by its surface tension in the pouring cup and the melt thus held is poured under pressure by pressurizing the chamber into the mold through the upper sprue to thereby make a casting.

13 Claims, 8 Drawing Figures

MELTING AND PRESSURE CASTING DEVICE

BACKGROUND OF THE INVENTION

1. Field of the Invention

This invention relates to a device adapted for melting and gas pressure casting.

The invention relates also to a resistance heating element suitably used for the device.

2. Prior Art

For example, centrifugal casting and pressure casting according to a lost wax process using precious metal, non-precious metal, etc. have heretofore been used for casting crown artificial teeth, artificial teeth, and the like. Out of the pressure casting, in the case of gas pressure, such a method has been employed in which the upper part of the pouring cup of a mold is covered by a water-bearing cap, and the water retained in the cap is gasified suddenly by the heat of molten metal to effect pressure casting by the steam pressure thus produced or compressed air.

As apparent from the method, the conventional gas pressure casting leaves the problem that it is primitive and depends much upon the skill and technical judgement of an operator, and is not so good in reproducibility as is generally expected.

SUMMARY OF THE INVENTION

In view of the problem described above, the invention provides a method capable of automatic and simultaneous melting of a casting material and pressure application of gas and pouring of the material and exact pressure casting with high reproducibility.

The invention is characterized in that even if the respective operations of melting and casting are combined, the device of the invention is so small in size as to permit placing thereof on a table, and in addition, setting of a mold in and parting thereof from the furnace unit is very easy. The device of the invention is also suitable for casting not only the metals or alloys mentioned above but also glass. This invention also provides a heating means free from nonuniform heating and easy to detect and control temperature and which form no oxide as a desirable electric heating means.

A detailed description will now be given of preferred embodiments of the invention.

DETAILED DESCRIPTION OF THE INVENTION

Figure 2:
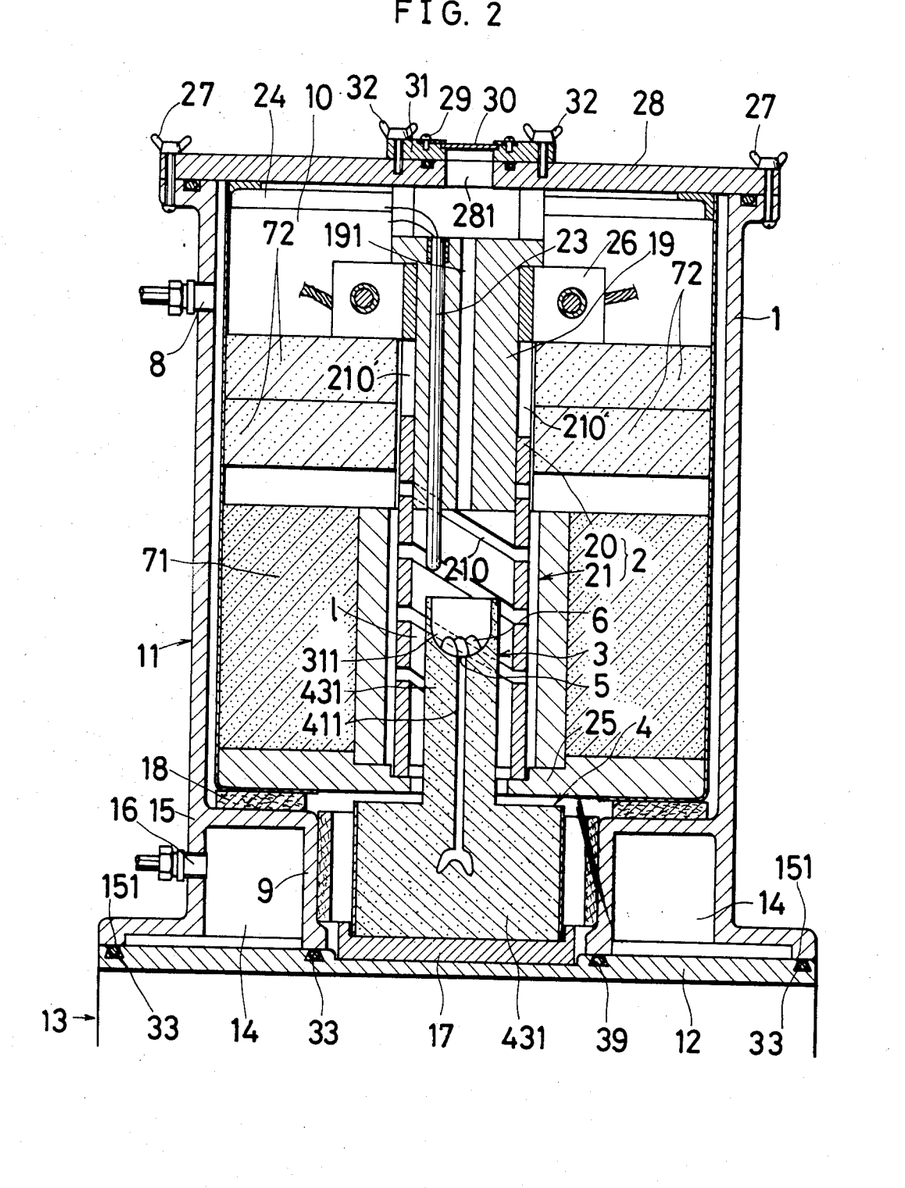
FIG. 2 is a longitudinal sectional front view showing the state in which a melting crucible and a mold inside a mold operating unit in FIG. 1 are elevated together with a table and have been set in a furnace.

The device of the invention, as shown in FIG. 2, comprises a cylindrical electric heating means 2 (hereinafter to be referred to simply as "a heating means") set in a closed chamber 1 adapted to be freely reduced and increased in gas pressure, a vertically long crucible 3 elevatable inside the heating means 2, a mold 4 connected below the crucible 3, and an upper sprue 5 communicating between the lower part of a pouring cup 311 of the crucible 3 and a sprue 411 of the mold 4, wherein when there is no substantial pressure difference in gas between the pouring cup 311 and the internal part of the mold 4, a casting melt 6 molten in the pouring cup 311 can stay without entering and falling in the upper sprue 5 by its surface tension. More particularly, the closed chamber 1 is a cylindrical chamber having a pressure reducing and increasing pipe 8 (hereinafter please refer to as inlet-outlet pipe) passing through the upper peripheral wall of the chamber 1 and having a small-diameter cylinder portion 9 in the lower part of the chamber. A heat insulating means 71 is placed in the chamber 1 encircling the cylindrical heating means 2 set in about the middle of the lower part of the chamber 1. The chamber 1 includes a furnace unit 11 including a gas passageway 10 communicating between the inlet-outlet pipe 8 and the inside of the heating means 2 and a table 12 which can come from below into contact with the diameter-reduced cylinder portion 9 in the lower part of the chamber 1. On the table 12 is placed the mold 4. A mold operating unit 13 is provided directly below the furnace unit 11, the unit 13 including the mold 4 and a vertically long crucible 3 extending upwardly of the mold 4, the crucible 3 including an upper sprue 5 communicating with the mold 4 and the sprue 411 of the mold 4, the upper sprue 5 opening into the lower part of the pouring cup 311. The crucible 3 is designed such that its pouring cup may be placed within the effective heating zone 1 (which zone will hereinafter be referred to as such, the zone including the vertical center of a heating portion 21 which, out of heating temperature distribution, indicates an especially high value and has an approximately uniform temperature) and the mold 4 may be placed within the cylinder portion 9 in the state of the table 12 being brought from below into contact with the small-diameter cylinder portion 9 and such that when there is no substantial difference in gas pressure between the upper sprue 411 and the inside of the mold 4, the casting melt 6 molten in the upper cup 311 is permitted to stay in the cup 311 by its surface tension without entering and falling in the upper sprue 5. When the bottom of the furnace unit 11 is closed with the table 12 and the mold 4 is set and pressure is applied to the mold for pressure casting, it is designed that the table 12 may not be detached from the furnace unit 11, namely, that a cylindrical wall 15 encircling the outside of the small-diameter portion 9 through a ringlike space 14 is provided in the lower part of the chamber 1 and a pressure-reducing and pressure-applying inlet-outlet pipe 16 passing through the wall 15 is attached thereto, and also when the chamber 1 is changed from reduced to increased pressure, the table 12 is enabled to be sucked to the bottom of the chamber 1 by reducing pressure inside the ringlike space independently of the chamber 1.

A further description will now be given of the invention with reference to FIG. 2. In FIG. 2, the numeral 17 designates a mold receiving bed for receiving and placing the mold 4 on the table 12. In the case shown, the bottom of the receiving bed 17 is placed through its flat surface on the table 12. It is sometimes desired to take it into consideration to make it difficult for the positive pressure in the chamber 1 to find its forced way into the mold 4 from the bottom of the mold 4 by forming the bottom of the bed 17 with a multi-stepped surface which provides an increased area of contact instead of the flat one and bring the multi-stepped surface into contact with the table 12. The numeral 18 designates a heat insulating material. Out of the insulating means 7, the lower one, for instance is of a ringlike insulating material 71 of ceramic fiber, and the upper one is of a heat insulating material 72 serving also to hold a heating means 2 concentrically. The material 72 is, for instance, formed likewise of ceramic fiber in a ringlike form by the use of a bonding agent. The heating means 2 is a ceramic resistance heating element (later described in detail) made of silicon carbide (SiC) and is provided below a cylindrical main body 20 with a resistance heating part 21 and the upper cup 311 of the crucible 3 and workpiece 6 (dental alloy material) are placed in the effective heating zone 1 of the heating means 2. The upper opening of the cylindrical main body 20 is sealed with a plug cover 19 provided in the center with a through hole and a thermocouple 23 adapted to detect the temperature in the resistance heating portion 21. The middle through hole 191 opens into an upper chamber cavity 24 of the insulating means 72. The lower end of the cylindrical main body 20 is held by a ring support 25 holding a heat insulating means 71 thereon, and the upper part of the body 20 is bound by a tight band 26. To the upper end opening of the chamber 1 is fixed a cover 28 by threaded fastening devices 27, and in the middle of the cover 28 is formed a peephole 281, and a peephole member 31 holding glass and other peephole plate 30 by screws 29 is attached to the peephole 281 by threaded fastening devices 32. The pouring cup 311 of the crucible 3 forms a convergently curved surface relative to the upper sprue 5, the curved surface being any one of oval curved surface, parabolic curved surface, arcuate curved surface and funnel-shaped curved surface. The diameter of the upper sprue 5, when there is no substantial pressure difference in gas between the crucible 3 and the mold 4, is selected in such a size as not to permit the melt 6 inside the pouring cup 311 to fall from the upper sprue 5 but to permit the same to stay therein. The embodiment in FIG. 2 shows the case wherein the crucible 3 and the mold 4 are formed integral with each other and wherein an investment 431 is used, extending over the crucible 3 and mold 4, but the case wherein the crucible 3 and the mold 4 are separate will later be described. An inlet-outlet pipe 8 is connected to a vacuum pump not shown. A cylindrical wall 15 is shown as extending to the base of the chamber 1 and being substantially L-shaped in section, and, when the table 12 is brought from below into contact with the lower end of a foot base 151 and the lower end of a diameter reduced cylindrical portion 9 through seal packings 33, respectively, a ringlike space 14 is closed and accordingly, when air is exhausted from another inlet-outlet pipe 16, the space 14 is reduced in pressure to thereby suck the table 12 to the foot base 151 and hold them in position.

Referring now, in FIG. 1, to a mold operating unit 13 placed immediately below the furnace unit 11, the operating unit 13 includes a desk-type base 34, left and right side frames 35, 36, an operating opening 37 formed between the base 34 and both frames 35, 36, a table 12 positioned in its lowermost position exposedly inside the opening 37 and adapted to be brought into a standby state for pouring a melt in its uppermost position as shown in FIG. 2, a mold receiving bed 17, a melting and casting member comprising a mold 4 and a crucible 3, and a lifting arm 38 for holding the members on a horizontal level and elevating the same, and coil springs 39 for resiliently holding the members horizontally. Arranged in front of the base 34 are switches and buttons such as an on-off power switch 40, arm raising and lowering switch 41, furnace temperature display 42, furnace temperature setter 43, temperature holding timer 44, pressure applying timer 45, pressure reduction setting knob 46, furnace pressure gauge 47, pressure setting knob 48, starting button 49, standby button 50, release button 51. Incidentally, the lifting arm 38 is elevated by an electric elevation mechanism (not shown).

In the above, mention is made of an example of elevating the table 12, but instead it may be possible to move up and down the chamber 1. As a heating means 2 are used various resistance heating elements, high frequency induction heating means, are discharge heating means, etc. but in the case of a material not only very high in melting temperature (1200°–1550° C.) such as a dental material (sometimes a nonprecious metal) but also readily oxidizable, heat is produced from the surface of a workpiece by skin effect in the case of high frequency induction heating, with the result that the surface is rendered overheated above the temperature inherently necessary for melting, and part of the alloy constituent is evaporated to spoil the property of the alloy. In addition, because temperature distribution is not uniform, temperature detection of a workpiece becomes incorrect, and the temperature control made on the basis of this incorrect temperature detection, in turn, becomes improper. This is a problem. Also, in the arc discharge heating, arc generating point alone in the workpiece is rendered partially high in temperature. This also entails a problem to be solved.

With respect to the melting material described above, the inventors have fully recognized that the resistance heating element of silicon carbide to be described later can solve the problem described. Namely, the SiC resistance heating element makes it easy to make temperature detection by heating the element under energization in the state of oxygen supply being cut off in the closed chamber to thereby cause an oxidation reaction of $SiC + 3/2O_2 \rightarrow SiO_2 + CO$ to decrease the amount of oxygen and to maintain the chamber in reducing atmosphere by produced CO and to prevent oxidation of a workpiece and heat the whole surface of the workpiece substantially uniformly by Joule heat under enclosure of the workpiece.

Figure 5:
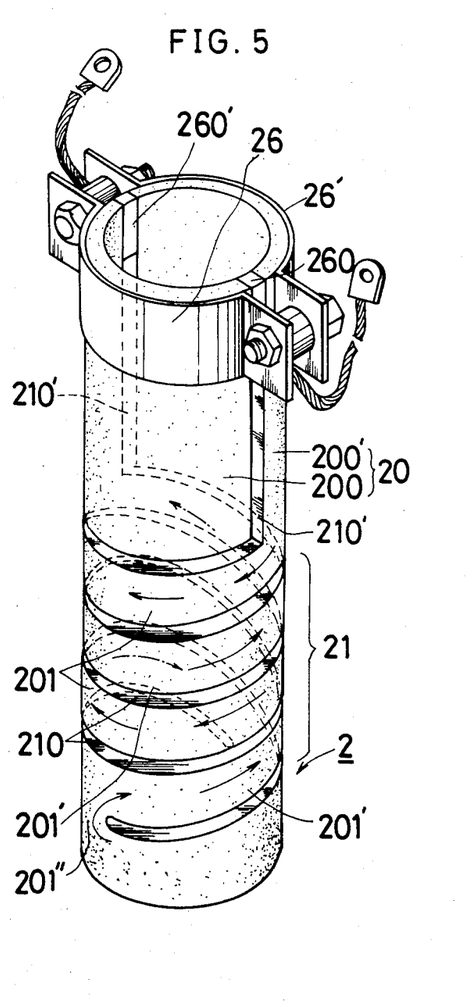
FIG. 5 is a perspective view of an embodiment of a SiC resistance heating element used in the invention.
Figure 6:
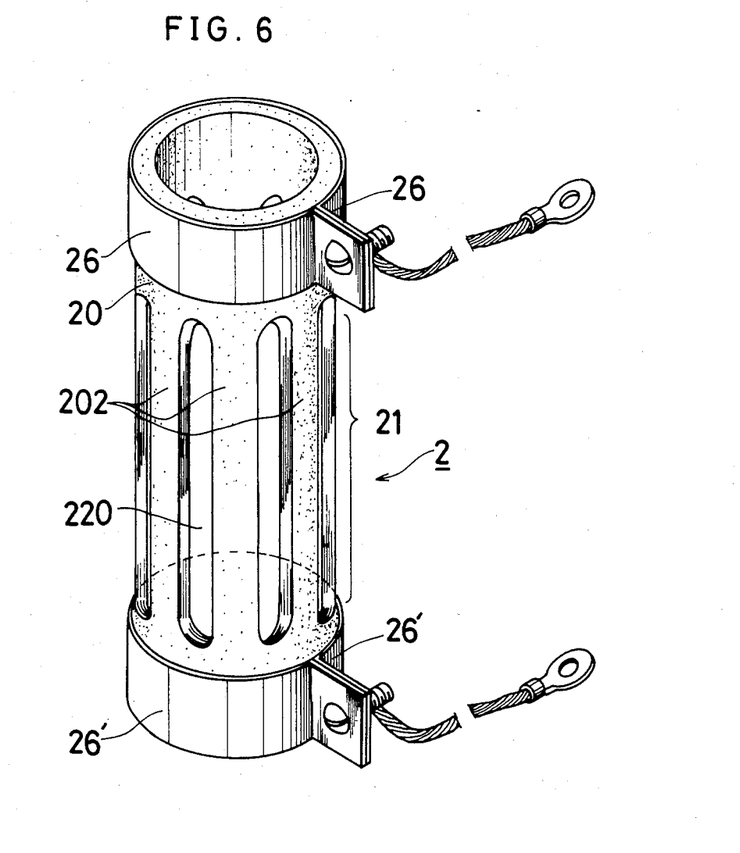
FIG. 6 is a perspective view of another embodiment of the SiC resistance heating element used in the invention.
Figure 7:
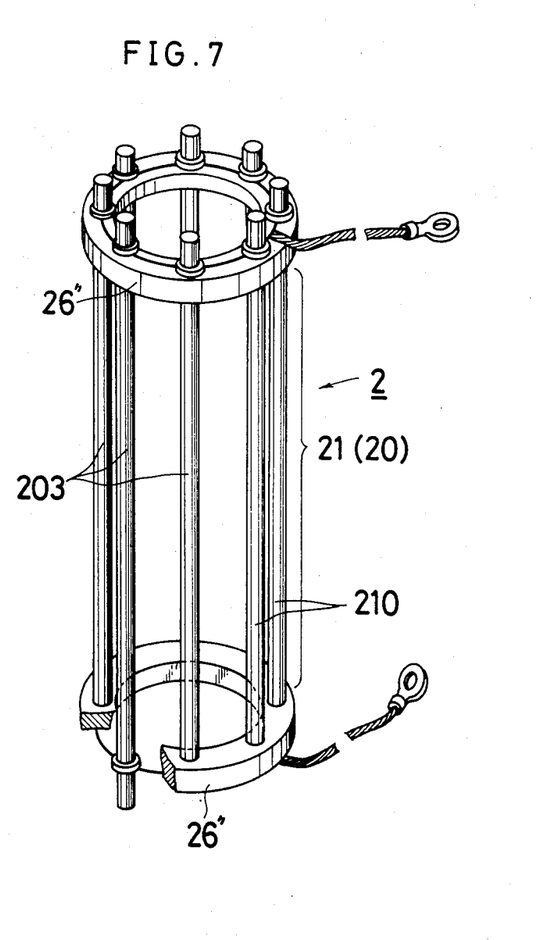
FIG. 7 is a perspective view of still another embodiment of the SiC resistance heating element.

Referring to this SiC resistance heating element with reference to the drawings, FIG. 5 shows a helical slot type resistance heating element; FIG. 6 a straight slot type; and FIG. 7 shows a multi-column slot type, respectively. The element in FIG. 5 is a cylindrical main body 20 of SiC sintered body formed vertically with a series of helical slots 210 including vertical slots 210′, 210' as shown. In the upper part of this body 20, the body 20 is sectioned into electrically insulated and separated half segments 200, 200' and electroconductive terminal semicircular bodies 26, 26' are placed on the upper parts of the half segments 200, 200' through insulating tips 260, 260' between the rings to join two half segments 200, 200' together, and below the half segments are formed a pair of helical rings 201, 201' insulatively sectioned by the helical slot 210 alternately with respect to the vertical direction of the segments and at the respective terminals of the helical rings 201, 201' are joined both rings 201, 201' together at 201''. As a result, when one half segment 200 is energized, the current flows from the helical ring 201 to the other half segment 200' through the helical ring 201' (the route of current flow is indicated by arrows). By this energization, Joule heat is concentrated on the helical rings 201, 201' of small area to form a heating portion 21. Heating temperature is for example in the range of 500°-1,800° C. In FIG. 6 showing another embodiment, a plurality of vertical straight slots 220 are provided in a cylindrical main body 20 made of SiC sintered body, and electroconductive terminal rings 26, 26' are fitted over the upper and lower parts of the body 20, respectively. In this case, straight paths 202 sectioned by the slots 220 forms a heating portion 21. In FIG. 7 showing still another embodiment, a plurality of vertical rods of SiC sintered body 203 are circumferentially set between upper and lower electroconductive terminal support rings 26'' and 26''', and the rods 203 themselves form a heating portion 21.

Figure 8:
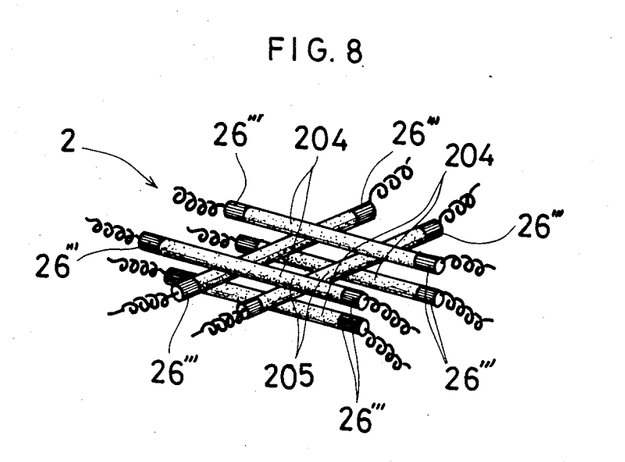
FIG. 8 is a perspective view of yet another embodiment of the SiC resistance heating element.

In the embodiment in FIG. 8, a plurality of rods 204 of SiC sintered body . . . provided at both ends with electroconductive terminals 26''', 26'''' are assembled in layers piled one over another in two parallel crosses and are electrically insulated one from another by placing insulating supports (not shown) between the upper and lower rods 204 . . . in the manner that heating portions near the middle of the rods 204, namely the parallelly crosswise assembled portions 205 may encircle the melting crucible (not shown). The SiC resistance heating element 2 of the embodiment thus constructed, because it permits vertical temperature distribution to concentrate in a greater degree only on the crucible and its neighborhood than the vertically arranged heating rods in FIG. 7, is suitable when it is necessary to hold a mold 4 portion in relatively low temperatures, and the element 2 further provides an additional advantage of reducing the distance between the crucible 3 and the mold 4. In addition, because the rods 204 . . . include no rigid supporting portions and are assembled merely in upper and lower layered relation, the possibility of production of crack and break due to thermal stress of the rods 204 . . . can greatly be reduced. The SiC resistance heating element 2 of the type described is placed in the described procedure in the enclosed chamber 1 which is freely reducible in pressure to decrease oxygen density. (The chamber shown is freely increasable in pressure because of pressure casting by gas.)

Next, a description will now be given of the procedure for operating a mold operating unit 13 to set a melting and casting member in a furnace unit 11 for melting and casting and then to take the member out of the unit 11.

Figure 1:
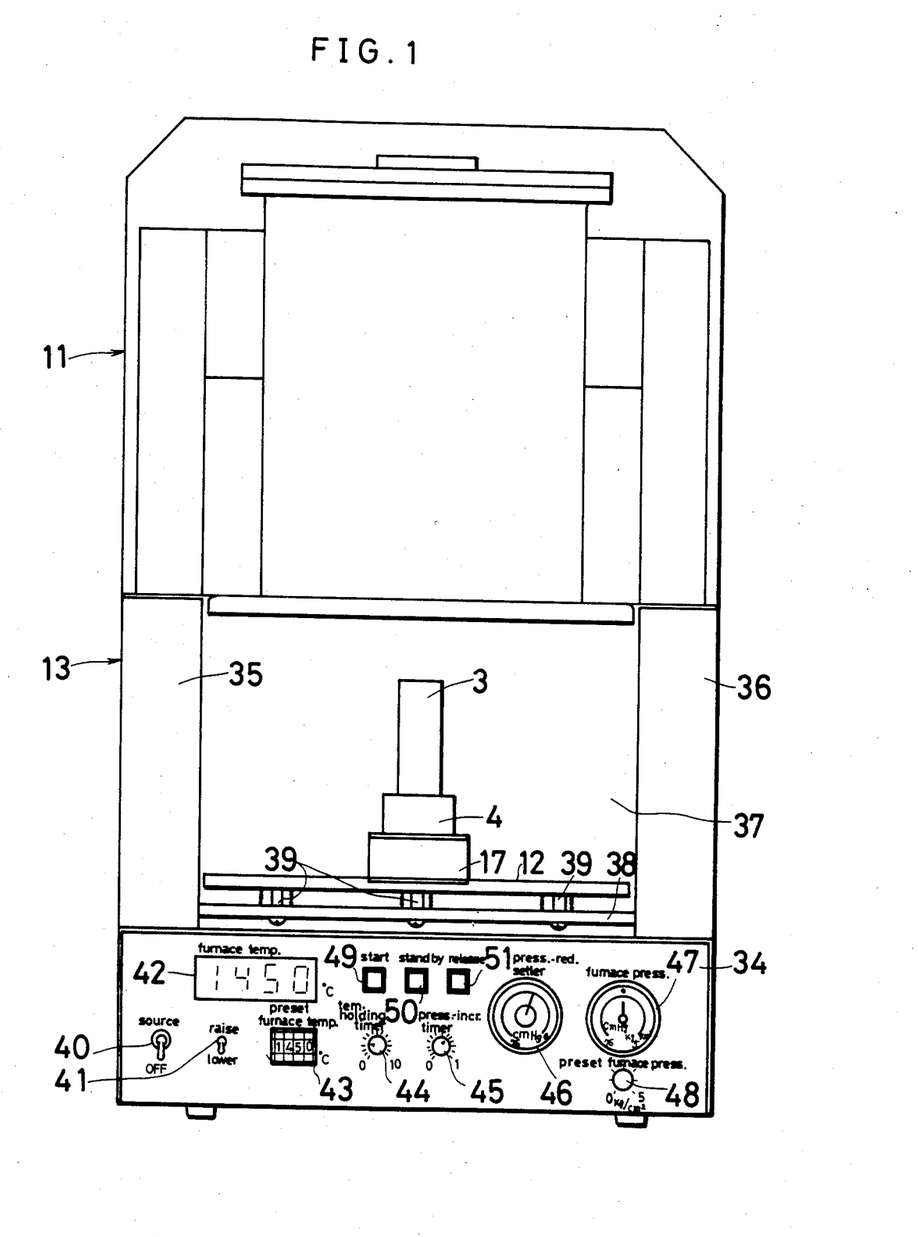
FIG. 1 is a front elevation of an embodiment of the invention.

(a) In the lowered position of the table 12 in FIG. 1, a power switch 40 is turned on. The heating means 2 of the furnace unit 11 starts heating. When the casting mold receiving bed 17 is placed on the table 12 and the table is elevated by a lift switch 41 for lifting the table onto the furnace unit 11 side, the inside of the furnace unit 11 is automatically heated to 350°-500° C. preliminarily (b) Casting temperture is set by a furnace temperature setter 43. The holding time of the temperature thus set is set by a temperature holding timer 44. The reduced pressure setting in the furnace during the holding time is effected by a knob 46. The pressure subsequent to release of pressure reduction is effected by a pressure setting knob 48.

(c) Next, when a standby button 50 is depressed, the temperature of the furance unit 11 is elevated to the set temperature. In setting the temperature, an indicator lamp (not shown), for example, is turned on and off.

(d) The table 12 is lowered by a table lowering switch 41 to place the mold 4 and crucible 3 thereon, and a metal (alloy), glass material, etc. for melting is charged into the pouring cup 311 of the crucible 3, and a starting button 49 is depressed. The table 12 is elevated to the furnace unit 11 by depression of the button 49, and the pressure in the furnace 11 is reduced to the preset pressure and the temperature is elevated to the set temperature and held at the temperature. When the holding time is over, the reduced pressure stops and casting is effected by application of pressure under the pressure and time previously set (usually by application of air but in the case of oxidizable metal by application of inert gas such as argon). When the casting is over, for example a buzzer is sounded and pressure is restored to a normalcy, and then the table 12 is lowered with the power switch 40 put into an ON-position. This pressure casting is carried out on a complete automatic basis. Reduction and increase in pressure are effected through the inlet-outlet pipe 8, while the pressure reduction and increase in the crucible 3 and mold 4 are effected through a gas passageway 10. On the other hand, until the table 12 starts being lowered, the ringlike space 14 sucks the table 12 to the lower end opening of the space 14 and holds the same with the space kept reduced in pressure independently of the chamber 1. And even when the mold 4 is pressurized, the space 14 prevents the table 12 from moving away from the opening downwardly. Discontinuation of pressure casting during standby treatment and automatic operation is effected by a release button 51. In the above operation, when the casting material is a dental crown, precious metal, nonprecious metal or castable ceramic is used, but it is apparent that materials other than those used in dental treatment are also used in pressure casting.

Figure 3:
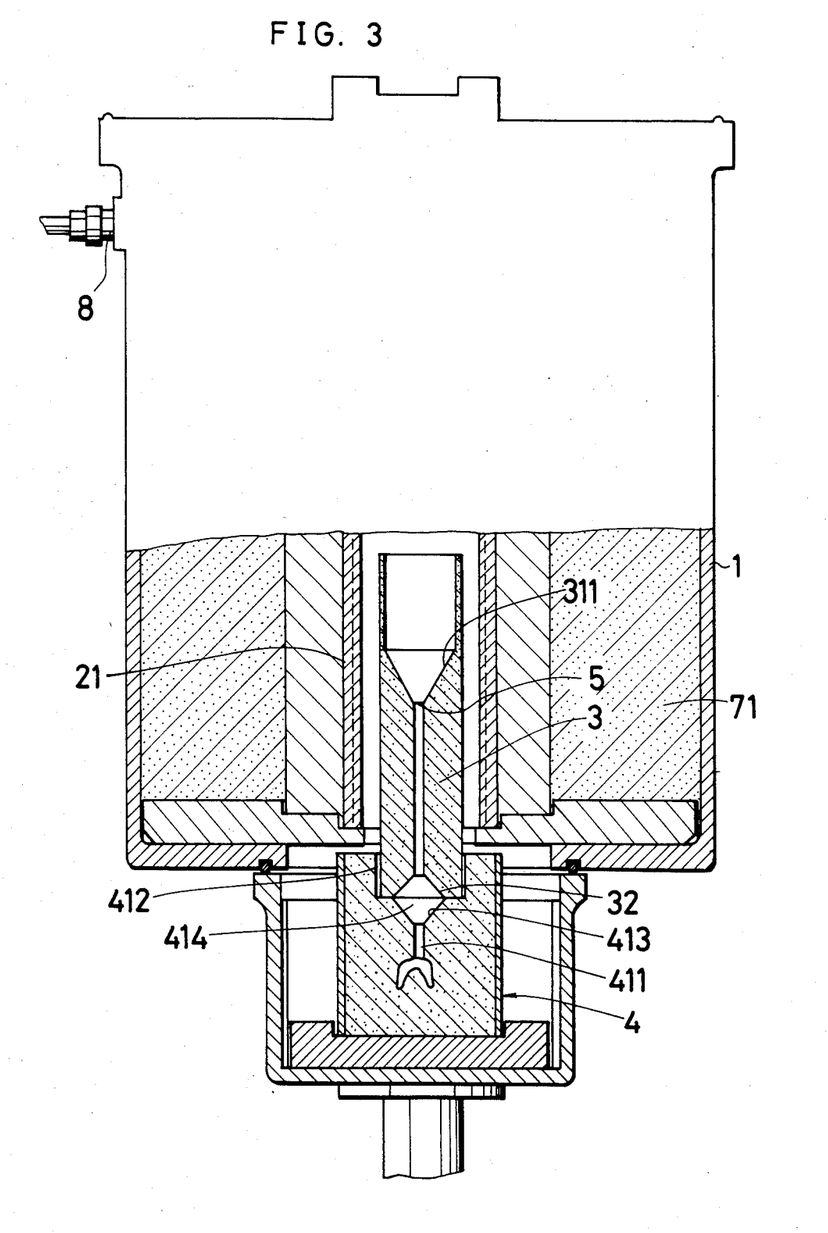
FIG. 3 is a longitudinal sectional front view, partly cutaway, of the essential part of an embodiment in which the crucible and the mold are separate.
Figure 4:
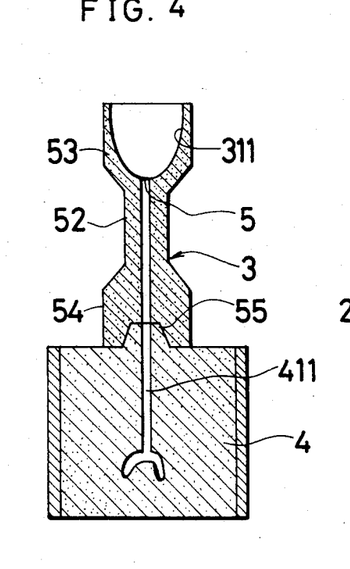
FIG. 4 is a longitudinal sectional front view showing exclusively the essential part of another embodiment of the crucible and the mold in FIG. 3.

In the embodiment shown in FIGS. 1 and 2 is shown the embodiment wherein the crucible 3 and mold 4 are formed integral with each other, while in FIG. 3 there is shown the embodiment wherein both the crucible 3 and the mold 4 are separate and wherein a molten metal reservoir is formed in the mold 4. As shown in the figure, a divergent opening 32 is formed in the lower end of the upper sprue 5 of a cylindrical crucible 3, a cylindrical recess 412 supporting the crucible 3 is formed in the upper end of the mold 4, and a convergent opening 413 corresponding to the divergent opening 32 is formed between the recess 412 and a sprue 411. When the crucible 3 and the mold 4 are connected, both openings 32 and 413 are formed between the upper sprue 5 and the sprue 411 to replenish an article of capacity with the molten metal of which the article runs short. The embodiment in FIG. 4 is similar to that in FIG. 3 wherein the crucible 3 and the mold 4 are separate. A difference of this embodiment from that of FIG. 3 is that the middle 52 of the crucible 3 is reduced in diameter and is small in heat capacity and the upper portion 53 and the lower portion 54 continued from the middle 52 are enlarged in diameter to decrease outward leak of radiant heat in the furnace and that the connecting portion 55 of the mold 4 is formed frusto-conical so as to prevent an investment of the crucible 3 in the connection between the crucible 3 and the mold 4 from entering the sprue 411 of the mold 4 when gas pressure is applied.

Now, a description will be given of operation and effect of the invention.

In the invention, when there is no substantial pressure difference in gas between the upper cup 311 and the inside of the mold 4, the melt 6 in the upper cup 311 of the crucible 3, because of its surface tension, stays in the cup 311 and keeps high fluidity by being kept placed under heating. But simultaneously with starting of application of pressure to the chamber 1, molten metal is poured into the mold 4 through the upper sprue 5 and sprue 411 at one stroke of operation and the metal is caused by positive pressure of gas from above to flow to the detail of the mold 4 so that casting of high dimensional accuracy can be made. It becomes possible to make casting not only with high heat efficiency under high pressure by moving up and down the crucible 3 within the heating means 2 and placing the same in an effective heating zone 1 of the means 2 but also with the least possible loss of heat during dropping of the melt 6 by connection of the crucible 3 with the mold 4. Also, pouring of the melt is carried out simultaneously with introduction of gas, with the result that casting high in reproducibility can be provided.

In the invention, the furnace unit 11 and the mold operating unit 13 are vertically connected, and in the unit 13 when the setting of the mold 4 and crucible 3 is over, they are automatically elevated for casting, and after the casting is over, they are lowered for taking out an article and are then reset, so that it becomes possible to carry out efficient pressure casting in a small space by utilizing a longitudinal space and saving a lateral space. Further, since in the invention even when the pressure in the furnace is changed from reduced to increased pressure, as long as the ringlike space 14 is placed under reduced pressure, the table 12 is not lowered by the increased pressure but is brought into tight contact with the underside of the furnace unit 11 and held in position, so that the invention provides the additional advantage of making it possible to hold the table 12 by a pressure-reducing procedure similar to the pressure-reducing procedure for the furnace unit 11 without the aid of an air cylinder, oil cylinder or the like.

Thus, the invention provides an excellent effect in that it has eradicated the drawback of the prior art being inferior in reproducibility in spite of the art requiring skill. On the other hand, when the SiC resistance heating element 2 is used, the element 2 is energized to generate heat in the state of air in the closed chamber 1 being extracted therefrom through an inlet-outlet pipe 8 and the oxygen density in the chamber being reduced and supply of new oxygen (i.e. air) being cut off. The surface of the heating element 2 is oxidized by heating and discharges CO gas into the chamber 1 through a reaction procedure for $SiC + 3/2O_2 \rightarrow SiO_2 + CO$. But because no fresh air is supplied to the chamber 1, the oxygen density in the chamber 1 is further reduced by proceeding of the above reaction, while SiC in the heating zone is degraded into $SiO_2$ in order and an amount of SiC is sequentially decreased. This phenomenon can be confirmed by formation of white SiC film on the surface of the SiC resistance heating element 2. As in the embodiment illustrated, when the enclosed chamber 1 is made freely reducible in pressure, it is desirable to keep oxygen density reduced prior to heat generation by energization. In the embodiment illustrated, after the workpiece 6 in the crucible 3 has been melted, air is introduced from an inlet-outlet pipe 8 into the chamber 1, and because the melt is subjected to pressure casting inside the lower mold 4 by the pressure of air thus introduced into the chamber, the oxygen density in the chamber 1 is greatly increased when the casting is over, but at that time, heating of the heat resistance element 2 has ceased and the melt has been poured into the mold 4 which is not subjected to heating, so that the melt is small in the degree of oxidation. In the embodiment, after each heating and casting are over, the chamber 1 is again set to the degree of reduced pressure in the aforestated scope and is used in the subsequent heating and casting.

In the case of any one of SiC resistance heating element 2 of the structure of four embodiments shown in FIGS. 5 to 8, the whole of the workpiece 6 is heated substantially uniformly and efficiently by the workpiece 6 being placed inside the heating portion 21 enclosed circumferentially of the heating element 2, especially being placed in an effective zone 1 showing a particularly high value out of heating temperature distribution. Accordingly, temperature detection in the heating portion, for example, detection by thermocouple 23 in FIG. 2 is easily and correctly carried out, with the result that temperature control in cooperative relation with this detection is also made properly. In the embodiment in FIG. 2, mention has been made of the case in which the resistance heating element 2 is arranged vertically, but it should be understood that the element 2 is not limited to that of the FIG. 2 embodiment, but may be arranged transversely as occasion demands.

As described, since the workpiece is heat treated in the closed chamber by the use of the SiC resistance heating element, it becomes possible to substantially prevent oxidation of the workpiece, irrespective of high temperature heating, by reducing atmosphere due to CO produced during the heat treatment without additionally using separate oxidation prevention means (e.g. a carbon material which is used as a reducing agent.) Accordingly, particularly it becomes possible to protect the workpiece against yellowing, deterioration in strength, change in composition, residual foams, incomplete filling in the mold, etc. due to the oxidation caused by high temperatures at which dental materials such as nonprecious metal, semi-precious metal, porcelain, and glass are melted. In addition, because the use of inert gas becomes unnecessary, the device is enabled to be simplified and heating of the workpiece is also carried out by heat from the whole circumference. Thus, the invention provides many distinct advantages in that it facilitates detection and control of temperatures.

Having described our invention as related to the embodiments shown in the accompanying drawings, it is our intention that the invention be not limited by any of the details of description, unless otherwise specified, but rather be construed broadly within its spirit and scope as set out in the accompanying claims.

What is claimed is:

1. A melting and pressure casting device comprising an electric heating means set in a closed chamber reducible and increasable in gas pressure, a crucible set in said heating means and having a pouring cup, a mold provided below said crucible and connected thereto and having a sprue therein, and an upper sprue communicating between the lower portion of said pouring cup and the sprue formed in the mold, wherein a molten melt for casting is held by its surface tension in the pouring cup, and the melt thus held is poured under pressure by pressurizing the chamber into the mold through the upper sprue to thereby make a casting, and further including a table in substantially airtight contact with the lower portion of said closed chamber, wherein said pouring cup is positioned within the effective heating zone of said heating means when said table is brought into contact with the lower portion of said chamber, said device being provided in the lower portion thereof with a ringlike space having a separate pressure reducing and increasing inlet-outlet pipe, said table being adapted to mount said crucible and mold thereon below said ringike space, wherein said space is designed to be reduced in pressure through the inlet-outlet pipe communicating with the space to thereby suck the table to the lower portion of the chamber and hold the table in position.

2. A melting and pressure casting device according to claim 1 wherein said crucible is formed integral with said mold.

3. A melting and pressure casting device according to claim 1 wherein said crucible and said mold are separately made and connected integrally with each other.

4. A melting and pressure casting device according to claim 1 wherein the pouring cup of the crucible is formed with a curved surface converging toward the opening of the upper sprue.

5. A melting and pressure casting device according to claim 4 wherein said curved surface of said pouring cup is any one of an ovally curved, parabolically curved or arcuately curved surfaces.

6. A melting and pressure casting device according to claim 1 wherein said electric heating means is a resistance heating element consisting of siicon carbide.

7. A melting and pressure casting device according to claim 6 wherein said resistance heating element of silicon carbide comprises an SiC sintered cylindrical body sectioned into two electrically insulated and separated half segments in the upper part of the body, both of said segments extending helically to form a continuous helical slot therebetween, and said segments being enclosed in the upper part thereof and tightened with electroconductive terminal semicircular bodies with insulative tips inserted therebetween and a pair of helical rings insulatively sectioned by the helical slots are alternately vertically arranged in the lower sides of the half segments and are connected together at the ends of the respective rings to provide a heating portion.

8. A melting and pressure casting device according to claim 6 wherein said resistance heating element of silicon carbide comprises a plurality of vertical straight slots formed in a cylindrical body and has electroconductive terminal rings mounted on the upper and lower portions of the body, the straight paths sectioned by the slots forming heating portions, respectively.

9. A melting and pressure casting device according to claim 6 wherein said resistance heating element of silicon carbide consists of a plurality of vertical rods of SiC resistance heating element set and held circumferentially between the upper and lower electroconductive terminal-support rings, said rods themselves forming heating portions, respectively.

10. A melting and pressure casting device according to claim 6 wherein said resistance heating element of silicon carbide comprises a plurality of rods of SiC sintered body having electroconductive terminals at both ends thereof, said rods being assembled in layers piled one over another in two parallel crosses and being electrically insulated one upper rod from another lower one, the thus parallelly crosswise assembled portions being adapted to encircle the crucible.

11. A casting device comprising:
a first chamber having a heating element;
a second chamber;
means for maintaining the relative position of said first and second chambers;
a platform having a surface thereon, said surface having a first portion capable of forming a substantially air-tight seal with said first chamber and a second portion capable of forming a substantially air-tight seal with said second chamber;
means for reducing pressure within said second chamber when said second portion of said surface forms said seal with said second chamber,
whereby the pressure differential created by said reduced pressure maintains said surface against said first chamber and said second chamber.

12. A device as in claim 11 wherein said means for maintaining the relative position of said first and second chambers comprises at least one wall which is common to both said first chamber and said second chamber.

13. A device as in claim 11 further comprising:
a mold;
a crucible;
said mold and said crucible being supported on said platform and being positioned within said first chamber when said first portion of said surface forms a substantially air-tight seal with said first chamber.

* * * * *